United States Patent
Schoen et al.

(10) Patent No.: US 6,773,499 B2
(45) Date of Patent: Aug. 10, 2004

(54) PIGMENT MIXTURE

(75) Inventors: Sabine Schoen, Darmstadt (DE); Reiner Vogt, Kranichstein (DE); Norbert Schül, Heppenheim (DE); Karl Osterried, Dieburg (DE); Johann Munz, Gross-Rohrheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/394,000

(22) Filed: Mar. 24, 2003

(65) Prior Publication Data

US 2003/0177950 A1 Sep. 25, 2003

Related U.S. Application Data

(62) Division of application No. 09/701,298, filed as application No. PCT/EP99/03423 on May 18, 1999, now Pat. No. 6,632,275.

(30) Foreign Application Priority Data

May 28, 1998 (DE) .......................................... 198 23 866

(51) Int. Cl.⁷ ............................ C09C 1/00; C09D 5/36; C09D 11/02; C08K 9/02; A61K 7/00
(52) U.S. Cl. ...................... 106/404; 106/31.9; 106/403; 106/415; 106/446; 106/457; 106/475; 106/479; 106/482
(58) Field of Search ................................ 106/31.9, 403, 106/404, 415, 446, 457, 475, 479, 482

(56) References Cited

U.S. PATENT DOCUMENTS

| | | |
|---|---|---|
| 5,277,711 A | 1/1994 | Schmidt et al. |
| 5,354,374 A | 10/1994 | Prengel |
| 5,441,564 A | 8/1995 | Vogt |
| 5,672,200 A | 9/1997 | Heinz et al. |
| 5,733,364 A | 3/1998 | Schmid et al. |
| 5,759,257 A | 6/1998 | Ambrosius et al. |
| 6,063,179 A | 5/2000 | Schmid et al. |
| 6,162,374 A | 12/2000 | Schoen et al. |
| 6,238,471 B1 | 5/2001 | Vogt et al. |
| 6,267,810 B1 | 7/2001 | Pfaff et al. |
| 6,280,520 B1 | 8/2001 | Andes et al. |
| 6,294,010 B1 | 9/2001 | Pfaff et al. |
| 6,334,893 B1 | 1/2002 | Pfaff et al. |
| 6,372,036 B1 * | 4/2002 | Pfaff et al. .................. 106/443 |
| 2002/0056399 A1 * | 5/2002 | Schoen et al. ............. 106/31.9 |

FOREIGN PATENT DOCUMENTS

| | | |
|---|---|---|
| DE | 42 40 511 | 6/1994 |
| DE | 196 14 636 | 10/1997 |
| DE | 196 14 637 | 10/1997 |
| EP | 562 329 | 9/1993 |
| EP | 803 550 | 10/1997 |
| WO | WO 93/08237 | 4/1993 |

* cited by examiner

*Primary Examiner*—Anthony J. Green
(74) *Attorney, Agent, or Firm*—Millen, White, Zelano, Branigan, P.C.

(57) ABSTRACT

The present invention relates to pigment mixtures consisting of at least two components, component A being $SiO_2$ flakes coated with one or more metal oxides and/or metals and component B being special-effect pigments, and to their use in varnishes, paints, printing inks, masterbatches, plastics and cosmetic formulations.

12 Claims, No Drawings

PIGMENT MIXTURE

This application is divisional of U.S. Ser. No. 09/701,298, filed Nov. 28, 2000 now U.S. Pat. No. 6,632,275.

The present invention relates to pigment mixtures consisting of at least two components, component A being $SiO_2$ flakes coated with one or more metal oxides and/or metals and component B being one or more coated or uncoated special-effect pigments, and to their use in varnishes, paints, printing inks, plastics and cosmetic formulations.

With platelet-shaped pigments, hiding power and gloss are often difficult to realize simultaneously to a satisfactory extent. For instance, $SiO_2$ flakes or mica platelets covered with one or more thin metal oxide layers feature interference colours and a high lustre but at the same time, owing to the transparent substrate, feature high transparency and hence a comparatively poor hiding power.

Thus EP 0 562 329 discloses a pigment mixture comprising iron oxide-coated aluminium flakes in combination with iron oxide-coated mica pigments.

DE-A-42 40 511 discloses a pigment mixture which consists of an interference pigment and a platelet-shaped colour pigment. The interference pigment comprises metal oxide-coated mica flakes or $SiO_2$ flakes, and the colour pigment can be coloured, uncoated $SiO_2$ flakes. This pigment mixture is incorporated into coating materials, printing inks or plastics.

The object of the present invention is to provide a pigment mixture which is notable for relatively high hiding power and which lends itself well to incorporation into the respective system in which it is used, and for which at the same time a separation of pigment/colourant in the system is largely ruled out.

Surprisingly, a pigment mixture has now been found which has none of the disadvantages indicated above. The pigment mixture of the invention consists of at least two components, component A being $SiO_2$ flakes coated with one or more metal oxides and/or metals and component B being one or more special-effect pigments. The admixture of the special-effect pigments to the coated $SiO_2$ flakes is able to give the systems in which they are used a multiple flop, the colour effect is intensified, and new colour effects are achieved.

The invention thus provides a pigment mixture consisting of at least two components, component A being $SiO_2$ flakes coated with one or more metal oxides and component B being one or more special-effect pigments.

The invention likewise provides the formulations, such as paints, varnishes, printing inks, plastics, agricultural films and cosmetic formulations, which comprise the pigment mixture of the invention.

The coated $SiO_2$ flakes can be mixed in any proportion with the special-effect pigments. The ratio of component A to component B is preferably from 1:10 to 10:1, in particular from 3:1 to 5:1.

The $SiO_2$ flakes preferably produced on a continuous belt in accordance with WO 93/08237 are based on a platelet-shaped, transparent matrix and generally possess a thickness of between 0.1 and 5 µm, in particular between 0.2 and 2.0 µm. The extent in the two other dimensions is usually between 1 and 250 µm, preferably between 2 and 100 µm and, in particular, between 5 and 40 µm. The $SiO_2$ flakes are provided with one or more metal oxide layers and/or metal layers. Examples of suitable metal oxides or metal oxide mixtures are titanium dioxide, zirconium oxide, zinc oxide, iron oxides and/or chromium oxide, especially $TiO_2$ and/or $Fe_2O_3$. The $SiO_2$ flakes can be coated as described, for example, in WO 93/08237 (wet chemical coating) or DE-A-196 14 637 (CVD process).

Instead of the outer metal oxide layer a semitransparent layer of metal can be used. Suitable metals for this are, for example, Cr, Ti, Mo, W, Al, Cu, Ag, Au and Ni. Prefered pigments have the following layer structure: $SiO_2$ flakes+metal+$SiO_2$+metal oxide.

To induce special colour effects, fine particles in the nanometre size range can be incorporated additionally into the metal oxide layers of high or low refractive index. Examples of suitable candidates are finely divided $TiO_2$ or finely divided carbon (carbon black) with particle sizes in the range 10–250 nm. A controlled influence can be exerted on lustre and hiding power by virtue of the light-scattering properties of such particles. Preferably, the $SiO_2$ flakes are coated with one or more metal oxides.

Suitable components B for the pigment mixture of the invention are all special-effect pigments familiar to the skilled worker in the effect pigment sector, examples being metal effect pigments, such as aluminium, copper, zinc, tin and their alloys. Aluminium and gold bronze alloys are preferably to be mentioned, especially those having a particle size of from 2 to 40 µm. The pigment mixtures of the invention preferably comprise coated platelet-shaped iron oxide, aluminium flakes or coated aluminium flakes. Special-effect pigments of this kind are marketed by BASF under the name Paliocrom®, by Eckart-Werke under the name Standard®, and by the company Flex. Mention should also be made of pearl lustre pigments, $Al_2O_3$ flakes coated with metal oxides, such as $TiO_2$ or $Fe_2O_3$, for example, graphite platelets, BiOCl or glass flakes.

Pearl lustre pigments, mica flake pigments coated with one or more metal oxides, are obtainable, for example, from Merck KGaA, Darmstadt, under the trade name Iriodin®. The latter pigments are known, for example, from the German Patents and Patent Applications 14 67 468, 19 59 998, 20 09 566, 22 14 545, 22 15 191, 22 44 298, 23 13 331, 25 22 572, 31 37 808, 31 37 809, 31 51 343, 31 51 354, 31 51 355, 32 11 602 and 32 53 017. Mica pigments coated with $TiO_2$ and/or $Fe_2O_3$ are employed in particular. As phyllosilicate both natural and synthetic mica are suitable.

The pigment mixture of the invention is simple and easy to handle. The pigment mixture can be incorporated into the system in which it is used by simple stirring. Laborious milling and dispersing of the pigments is not necessary.

The pigment mixture of the invention can be used for pigmenting coating materials, printing inks, plastics, agricultural films, button pastes, for the coating of seed, for the colouring of food, coatings of medicaments or cosmetic formulations. The concentration of the pigment mixture in the system in which it is to be used for pigmenting is generally between 0.01 and 50% by weight, preferably between 0.1 and 5% by weight, based on the overall solids content of the system. This concentration is generally dependent on the specific application.

Plastics comprising the pigment mixture of the invention in amounts of from 0.1 to 50% by weight, in particular from 0.5 to 7% by weight, are frequently notable for a particular sparkle effect.

In the coating sector, especially in automotive finishing, the pigment mixture is employed in amounts of 0.5–10% by weight. The proportion in which the coated $SiO_2$ flakes are mixed with component B, especially coated or uncoated aluminium flakes, depends on the desired effect. The $SiO_2$ flakes are preferably employed with component B in a ratio of 5:1, in particular of 3:1.

In the coating material, the pigment mixture of the invention has the advantage that the desired colour flop effect is obtained by a single-layer coating (one-coat systems or as a basecoat in a two-coat system). This colour flop is extremely pronounced even under diffuse light. In comparison with coatings which comprise an intererence pigment rather than the coated $SiO_2$ flakes, coatings with the pigment mixture of the invention exhibit a marked depth effect and a glitter effect and also a strong colour flop.

In the pigmentation of binder systems, for example for paints and printing inks for intaglio, offset or screen printing, pigment mixtures consisting of coated $SiO_2$ flakes with Stapa®—aluminium and gold bronze pastes from Eckart-Werke—have proven particularly suitable. The pigment mixture is incorporated into the printing ink in amounts of 2–50% by weight, preferably 5–30% by weight and, in particular, 8–15% by weight. The mixing ratio of component A to component B is preferably in the range from 1:10 to 10:1. The printing inks comprising the pigment mixture of the invention exhibit purer hues and are of improved printability owing to the good viscosity values.

The invention likewise provides pigment preparations comprising coated or uncoated $SiO_2$ flakes, metal effect pigments, binders and, if desired, additives, the said preparations being in the form of substantially solvent-free, free-flowing granules. Such granules contain up to 95% by weight of the pigment mixture. A pigment preparation in which the pigment mixture of the invention is pasted up with a binder and with water or an organic solvent, with or without additives, and the paste is subsequently dried and brought into a compact particulate form, e.g. granules, pellets, briquettes, a masterbatch or tablets, is particularly suitable as a precursor for printing inks.

The present invention therefore also provides formulations comprising the pigment mixture of the invention.

The examples which follow are intended to illustrate the invention without, however, limiting it.

EXAMPLES

Example 1

Paint

Formulations consisting of

| | |
|---|---|
| 2.50% | $Fe_2O_3$-coated $SiO_2$ flakes having a particle size of 5–40 μm (Merck KGaA) |
| 1.50% | Monastral green 6Y spec. (Zeneca) |
| 0.50% | Cappoxyt yellow 4214 (Cappelle) |
| 0.03% | Pigment-grade carbon black FW 200 (Degussa) |
| 0.40% | Dollaraluminium Alpate 7620 NS (Alcan Toyo Europe) |
| Remainder: | Paint base with 19% solids content (acrylate-melamine) and diluent mixture |

Example 2

Intaglio Printing

Printing ink consisting of

| | |
|---|---|
| 70 g | of nitrocellulose-based binder from Gebrüder Schmidt, 95MB011, with solids content of about 20% |
| 30 g | of pigment, i.e. 15 g of Cromal IV (Eckart) AL 14–18 μm and 15 g of $Fe_2O_3$-coated $SiO_2$ flakes of particle size 5–40 μm |
| 30 g | of 1-ethoxy-2-propanol |

Example 3

Plastic 1 kg of polystyrene granules are wetted uniformly in a tumble mixer with 5 g of adhesion agent. Then 35 g of $Fe_2O_3$-coated $SiO_2$ flakes of particle size 5–40 μm and 7 g of Iriodin® 121 $TiO_2$-coated mica pigment from Merck KGaA, Darmstadt, FRG with particle size 5–20 μm are added and the components are mixed for 2 minutes.

These granules are processed under customary conditions on an injection moulding machine to give small stepped plates measuring 4×3×0.5 cm. The small stepped plates are notable for their lustre.

Example 4

Eyeshadow

| | |
|---|---|
| Phase A | |
| 15.00% | $TiO_2$-coated $SiO_2$ flakes of particle size 5–40 μm (Merck KGaA) |
| 15.00% | Timiron Super Blue ($TiO_2$-coated mica of particle size 10–60 μm from Merck KGaA) |
| 49.50% | Talc |
| 7.50% | Solanum Tuberosum (potato starch) |
| 2.50% | Magnesium stearate |
| Phase B | |
| 9.14% | Isopropyl stearate |
| 0.53% | Cetyl palmitate |
| 0.53% | Petrolatum |
| 0.21% | Fragrance |
| 0.11% | Preservative |

The constituents of Phase A are combined and formed into a premix. The melted chase B is then added dropwise with stirring to the powder mixture. The powders are pressed at 40–50 bar.

Example 5

Shower Gel

| | |
|---|---|
| Phase A | |
| 0.10% | $TiO_2$-coated $SiO_2$ flakes of particle size 5–40 μm (Merck KGaA) |
| 0.10% | Timiron Super Blue ($TiO_2$-coated mica of partcle size 10–60 μm from Merck KGaA) |
| 0.75% | Xantham gum |
| ad 100.00% | Aqua |
| Phase B | |
| 20.00% | Decyl glycoside |
| 6.65% | Texapon ASV Sodium laureth sulfate Magnesium laureth sulfate Sodium laureth 8-sulfate Magnesium laureth 8-sulfate Sodium oleth sulfate Magnesium oleth sulfate |
| 0.20% | Preservative |
| 0.05% | Fragrance |
| Phase C | |
| 0.15% | Citric acid |
| 10.00% | Aqua |

For Phase A, the pigment is stirred into the water. The xanthan gum is scattered in slowly with stirring and the mixture is stirred until the gum has dissolved. Phases B and C are added in succession, and slow stirring is continued until all of the components are homogeneously distributed.

What is claimed is:

1. A composition comprising a binder and a pigment mixture,
    wherein the pigment mixture comprises two different components A and B mixed in a weight ratio of A:B of from 1:10 to 10:1, wherein component A is $SiO_2$ flakes coated with one or more metal oxides and/or metals and component B is a special effect pigment comprising one or more of metal platelets optionally coated with one or more metal oxides, graphite platelets, optionally coated aluminum platelets, optionally coated phyllosilicates, optionally coated $Al_2O_3$ flakes, $Fe_2O_3$ flakes, $TiO_2$ flakes, BiOCl, glass platelets and ceramic platelets, and
    wherein the composition is substantially solvent-free and in the form of free-flowing granules.

2. The composition of claim 1, wherein component A comprises a pigment of $SiO_2$ flakes coated with $TiO_2$ and/or $Fe_2O_3$.

3. The composition of claim 1, wherein components A and B are mixed in a weight ratio of A:B of from 3:1 to 5:1.

4. The composition of claim 1, wherein the component B special effect pigment comprises optionally coated aluminum platelets.

5. The composition of claim 1, wherein the component B special effect pigment comprises a gold/bronze alloy pigment.

6. The composition of claim 1, wherein the component B special effect pigment comprises an optionally coated platelet-shaped iron oxide pigment, aluminum flakes or coated aluminum flakes.

7. The composition of claim 1, wherein the component B special effect pigment comprises optionally coated $Al_2O_3$ flakes, graphite platelets, BiOCl or glass platelets.

8. The composition of claim 1, wherein the component B special effect pigment comprises a pearl luster pigment of mica coated with one or more metal oxides.

9. The composition of claim 1, wherein the component B special effect pigment comprises aluminum flakes or coated aluminum flakes.

10. The composition of claim 1, wherein the component B special effect pigment comprises optionally coated $Al_2O_3$ flakes, BiOCl or glass platelets.

11. The composition of claim 1, wherein the composition contains up to 95% by weight of the pigment mixture.

12. A paint, varnish, printing ink, powder coating, masterbatch, plastic, colored seed coating, cosmetic or food coloring enhancer comprising a composition according to claim 1.

* * * * *